United States Patent

Onishi et al.

Patent Number: 5,670,558
Date of Patent: Sep. 23, 1997

[54] MEDICAL INSTRUMENTS THAT EXHIBIT SURFACE LUBRICITY WHEN WETTED

[75] Inventors: Makoto Onishi, Kanagawa; Kenichi Shimura, Tokyo; Naoki Ishii, Kanagawa, all of Japan

[73] Assignee: Terumo Kabushiki Kaisha, Shibuya-ku, Japan

[21] Appl. No.: 498,796

[22] Filed: Jul. 6, 1995

[30] Foreign Application Priority Data

| Jul. 7, 1994 | [JP] | Japan | 6-155860 |
| Jul. 8, 1994 | [JP] | Japan | 6-157715 |
| Jul. 15, 1994 | [JP] | Japan | 6-164254 |
| Jul. 18, 1994 | [JP] | Japan | 6-165508 |
| Jul. 22, 1994 | [JP] | Japan | 6-170529 |

[51] Int. Cl.$^6$ .............. A01N 1/00; A61F 2/00; A61M 5/32

[52] U.S. Cl. .............. 523/112; 523/105; 523/113; 523/122; 604/265

[58] Field of Search .............. 523/112, 105, 523/113, 122; 604/265

[56] References Cited

U.S. PATENT DOCUMENTS

| 4,100,309 | 7/1978 | Micklus et al. | 427/2 |
| 4,119,094 | 10/1978 | Micklus et al. | 128/132 R |
| 4,373,009 | 2/1983 | Winn | 428/424.2 |
| 4,459,317 | 7/1984 | Lambert | 427/2 |
| 4,487,808 | 12/1984 | Lambert | 428/423.1 |
| 4,666,437 | 5/1987 | Lambert | 604/265 |
| 4,876,126 | 10/1989 | Takemura et al. | 428/35.7 |
| 5,079,093 | 1/1992 | Akashi et al. | 428/411.1 |
| 5,091,205 | 2/1992 | Fan | 427/2 |
| 5,135,516 | 8/1992 | Sahatjian et al. | 604/265 |

FOREIGN PATENT DOCUMENTS

| 0 166 998 | 1/1986 | European Pat. Off. |
| 0 389 632 A1 | 10/1990 | European Pat. Off. |
| 0 611 576 A1 | 8/1994 | European Pat. Off. |
| 60-241448 | 11/1985 | Japan . |
| 6-7426 | 6/1994 | Japan . |
| 2 064 556 | 6/1981 | United Kingdom . |
| 2 190 387 | 11/1987 | United Kingdom . |
| 93/11751 | 6/1993 | WIPO . |

*Primary Examiner*—Thurman K. Page
*Assistant Examiner*—Kathryne E. Shelborne
*Attorney, Agent, or Firm*—Burns, Doane, Swecker & Mathis, LLP

[57] ABSTRACT

This invention provides a medical instrument having on a surface a layer (surface lubricating layer) that forms a hydrogel when wetted and that is composed of an insolubilized water-soluble or water-swellable polymer having a reactive functional group in the molecule. The surface having outstanding surface lubricity and, optionally, the ability to prevent the formation of thrombi.

7 Claims, 5 Drawing Sheets

MEDICAL INSTRUMENTS THAT EXHIBIT SURFACE LUBRICITY WHEN WETTED

BACKGROUND OF THE INVENTION

This invention relates to medical instruments having outstanding surface lubricity and, optionally, the ability to prevent the formation of thrombi.

In order to reduce the chance of damaging tissues such as blood vessels or to improve manipulation for accessing a target site, catheters and other medical instruments generally use low-friction materials on the matrix surface. Alternatively, in order to reduce the friction on the surface of a certain material, it is coated with a lubricant, a low-friction resin, a hydrophilic polymer, etc. For example, fluororesins and polyethylene resins are used as low-friction matrices, or fluororesins, silicone resins, silicone oil, olive oil, glycerin, etc. are applied to the surfaces of certain materials. However, most of these methods are not completely satisfactory in terms of safety and persistent efficacy because the lubricating substances will dissociate, separate (exfoliate) or dissolve away from the matrix surface.

Practical considerations have motivated recent studies on the approach of coating hydrophilic polymers. For example, U.S. Pat. No. 4,100,309 teaches a method of coating a hydrophilic polymer (polyvinyl pyrrolidone) using an isocyanate. It has also been proposed that an isocyanate be used in coating a hydrophilic polymer copolymerized with reactive functional groups (JPA 84/81341) or coating polyethylene oxide (JPA 83/193766). JPB 89/55023 teaches a method in which a copolymer of polyether, polyamide, polysiloxane or the like is bound, via polyisocyanate, to a surface having at least one group selected from among amino, imino, carboxyl and mercapto groups.

Additionally, WO 90/01344 teaches a method in which a polymer having a reactive functional group is applied onto a substrate surface, followed by coating with a hydrophilic polymer having a functional group capable of reacting with said reactive functional group.

JPB 89/33181 teaches a method in which reactive functional groups present on the matrix surface of a medical instrument are bonded covalently with a maleic anhydride based polymer so as to impart lubricity to the matrix surface.

These conventional methods of providing lubricating surfaces have not been satisfactory in terms of having properties since two kinds of compounds, an isocyanate compound and a hydrophilic polymer, have to be coated uniformly or because a plurality of coating operations are necessary (one for coating a crosslinking compound such as polyisocyanate and the other for coating a hydrophilic polymer). Additionally, compounds having more than one reactive functional group such as an isocyanate group in the molecule have such high reactivity that they will readily react with aerial moisture or impurities and this has presented various drawbacks including not only cumbersomeness in process control and the management of chemicals but also toxicity to humans.

Another factor that need be considered is the blood compatibility of lubricating surfaces. Thrombus formation and the activation of platelets will degrade the functions of medical instruments or lead to the manifestation of complications in the living body and, hence, medical instruments are required to possess surfaces having good compatibility with blood. However, many of the conventional lubricating surfaces do not have satisfactory ability to prevent the formation of thrombi. Even if they are effective to some extent in preventing thrombus formation, the lubricating layers do not have sufficient strength or slipping property to insure smooth passage through complexly bent blood vessels.

SUMMARY OF THE INVENTION

The present invention has been accomplished under these circumstances and has as an object providing medical instruments having outstanding surface lubricity and, optionally, the ability to prevent the formation of thrombi.

Another object of the invention is to provide simple processes for the manufacture of those medical instruments.

These objects of the invention can be attained in the following five aspects.

According to its first aspect, the invention provides a medical instrument having on a surface a layer (surface lubricating layer) that forms a hydrogel when wetted and that is composed of an insolubilized water-soluble or water-swellable polymer having a reactive functional group in the molecule.

Preferably, a process for producing the medical instrument is provided which comprises coating the matrix surface of the medical instrument with a solution containing a water-soluble or water-swellable polymer having a reactive functional group in the molecule and insolubilizing (crosslinking) said water-soluble or water-swellable polymer to form a layer on the surface of the medical instrument that will form a hydrogel when wetted.

Preferably, a process is provided wherein said water-soluble or water-swellable polymer is a block or graft copolymer having the reactive functional group selected from the group consisting of epoxy group, acid chloride group, aldehyde group and isocyanate group, and said block or graft copolymer is formed before it is coated on the matrix surface and the applied coating is heated at 40° C. or more to cure said copolymer to an extent that is determined by the required balance between the durability and water swellability of the cured film such that the cured film will form a hydrogel when wetted with water.

Preferably, a process is provided wherein said block or graft copolymer is formed from at least one monomer selected from the group consisting of glycidyl acrylate, glycidyl methacrylate, acrylamide, vinyl pyrrolidone and (meth)acrylic acid.

According to its second aspect, the invention provides a medical instrument exhibiting surface lubricity when wetted, characterized by having a surface lubricating layer that is composed of a crosslinked water-soluble or water-swellable polymer or a macromonomer and that forms an interpenetrating network structure on the matrix surface of the medical instrument.

Preferably, a process for producing the medical instrument is provided which comprises dipping a substrate of a medical instrument in a solution of water-soluble or water-swellable polymer or a macromonomer in a solvent which is swellable onto the substrate;

heating at 40° C. or more to form an interpenetrating network structure between the matrix surface of the medical instrument and said polymer or macromonomer to form a surface lubricating layer having superior peeling resistance in which said polymer or macromonomer is securely fixed to the matrix.

Preferably, a process for producing the medical instrument is provided wherein the matrix surface of the medical instrument is immersed in the solvent such that said matrix surface will swell by a factor of 1–100% as defined by the following equation (1):

$$\text{Percent swell} = \frac{\Delta W/\text{density of the solvent}}{Wo/\text{density of the matrix}} \times 100 \qquad (1)$$

According to its third aspect, the invention provides a medical instrument exhibiting surface lubricity when wetted, characterized in that an insolubilized matter comprising a water-soluble or water-swellable polymer having a reactive functional group and a polymer having a functional group capable of reacting with said reactive functional group binds to the matrix surface of the medical instrument to form a surface lubricating layer.

Preferably, a process for producing the medical instrument is provided which comprises preparing a polymer solution having dissolved in a solvent a mixture of said water-soluble or water-swellable polymer having a reactive functional group and said polymer having a functional group capable of reacting with said reactive functional group, impregnating said polymer solution in the matrix surface of the medical instrument and subsequently insolubilizing the impregnated polymer solution to form a surface lubricating layer on the surface of the medical instrument.

Preferably, a process for producing the medical instrument is provided which comprises preparing a first polymer solution having dissolved in a solvent said water-soluble or water-swellable polymer having a reactive functional group, impregnating said first polymer solution in the matrix surface of the medical instrument, preparing a second polymer solution having dissolved in a solvent polymer having a functional group capable of reacting with said reactive functional group, impregnating said second polymer solution in the matrix surface of the medical instrument, and subsequently insolubilizing the impregnated polymer solutions to form a surface lubricating layer on the surface of the medical instrument.

Preferably, a process is provided wherein said reactive functional group is at least one selected from the group consisting of epoxy group, acid chloride group, aldehyde group and isocyanate group and said functional group capable of reacting with said reactive functional group is at least one selected from the group consisting of carboxyl group, hydroxyl group, amino group, anhydrous carboxylic acid group and thiol group.

According to its fourth aspect, the invention provides a medical instrument having a surface lubricating layer which exhibits surface lubricity when wetted, characterized in that a solution having dissolved therein both a polymer which is the same as the polymer of which the matrix of the medical instrument is made or a component of the polymer of which the matrix of the medical instrument is made and a water-soluble or water-swellable polymer is coated on the matrix surface of the medical instrument.

According to its fifth aspect, the invention provides:

1) a medical instrument which forms a hydrogel layer on the outer surface when wetted, characterized in that the matrix of the medical instrument which is single- or multi-layered and has a polyolefin or modified polyolefin based layer disposed as at least the outer layer has a surface lubricating layer (a) formed on the outer surface, which is based on a mixture of a resin capable of bonding to said polyolefin or said modified polyolefin and an insolubilized water-soluble or water-swellable polymer having a reactive functional group; or 2) a medical instrument which forms a hydrogel layer on the outer surface when wetted, characterized in that the matrix of the medical instrument which is single- or multi-layered and has a polyolefin or modified polyolefin based layer disposed as at least the outer layer has an adhesive layer (a) and a surface lubricating layer (b) formed on the outer surface, which layer (a) is based on a resin capable of bonding to said polyolefin or said modified polyolefin and which layer (b) joins to said adhesive layer (a) and is based on an insolubilized water-soluble or water-swellable polymer having a reaction functional group.

Preferably, a process is provided wherein the matrix is a polyolefin-based matrix and wherein said block or graft polymer as mixed with an adhesive capable of bonding to a polyolefin is coated on the matrix surface and then cured or said adhesive is first coated on the matrix surface, then overcoated or overlaid with said block or graft copolymer and subsequently cured.

Further, in any one of the above first to fifth aspects, a medical instrument is provided wherein said surface lubricating layer further comprises an antithrombotic agent.

DETAILED DESCRIPTION OF THE INVENTION

Figure 1:
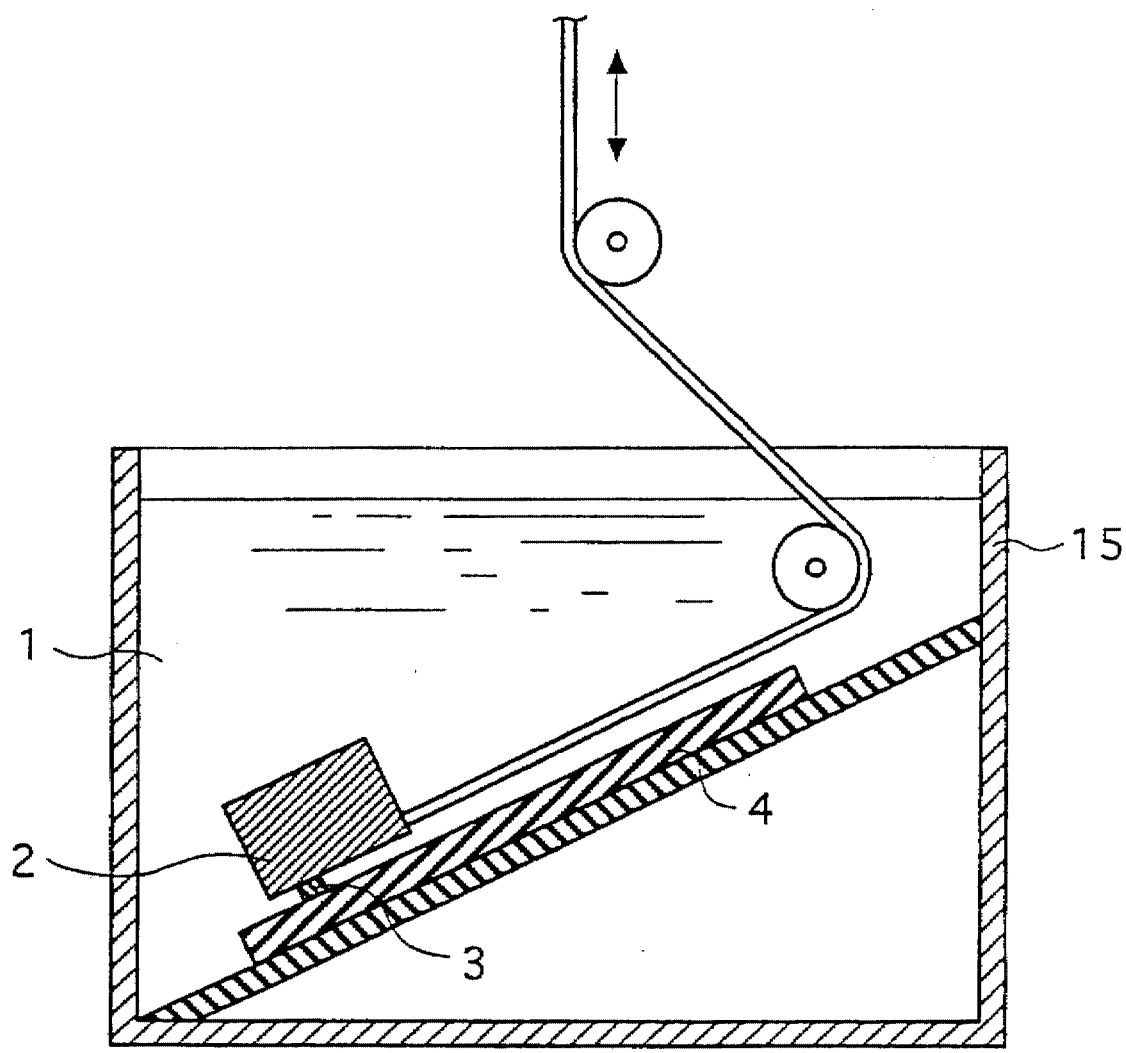
FIG. 1 is a schematic drawing of a surface lubricity meter.

According to the present invention:

(1) a surface lubricating layer comprising an insolubilized water-soluble or water-swellable polymer having a reactive functional group in the molecule is formed on the surface of the matrix of a medical instrument;

(2) a surface lubricating layer comprising an insolubilized (crosslinked) product of a water-soluble or water-swellable polymer having a reactive functional group in the molecule or a macromonomer is formed on the surface of the matrix of a medical instrument in such a way that said surface lubricating layer forms an interpenetrating network structure with the surface of the matrix;

(3) a surface lubricating layer comprising an insolubilized mixture of a water-soluble or water-swellable polymer having a reactive functional group in the molecule and a polymer having a functional group capable of reacting with said reactive functional group is formed on the surface of the matrix of a medical instrument;

(4) a surface lubricating layer comprising both a polymer which is the same as the polymer of which the matrix of a medical instrument is formed or a component of that polymer and a water-soluble or water-swellable polymer is formed on the surface of the matrix of said medical instrument; or (5) a surface lubricating layer comprising an adhesive polymer and a water-soluble or water-swellable polymer having a reactive functional group in the molecule is formed on the surface of the matrix of a medical instrument that is made of a polyolefin or a modified polyolefin.

If an antithrombotic agent is incorporated in any one of these surface lubricating layers, the layers will have low-friction properties for an almost indefinite period within body fluids or aqueous solvents and, additionally, they exhibit an outstanding antithrombotic action; hence, medical instruments having those surface lubricating layers will experience only small resistance when inserted into the windpipe, digestive tracts, urethra, blood vessels and other body cavities or tissues and this contributes to better access or manipulation, reduced damage to the tissue mucosas and abatement of the pain in patients. Particularly advantageous applications of the invention are to catheters and guide wires intended for use in blood vessels.

[1] The first aspect of the invention will now be described. In this aspect, a solution containing a water-soluble or water-swellable polymer having a reactive functional group in the molecule is coated on the matrix surface of a medical instrument and, thereafter, the water-soluble or water-swellable polymer is insolubilized to form a layer on the surface of the medical instrument that will form a hydrogel when wetted.

The matrix of the medical instrument is in no way limited and may be selected from among metals, ceramics, organic materials and composite materials, provided that organic polymer compounds are preferably present on the matrix surface. The matrix may be shaped from such polymers, alone or the latter may be shaped by copolymerizing or blending polymers so that they are present on the matrix surface. Exemplary organic polymer materials include polyolefins, modified polyolefins, polyethers, polyurethanes, polyamides, polyimides, polyesters and copolymers thereof. More preferred are those materials which have no functional groups that react with the reactive functional groups in the water-soluble or water-swellable polymer.

The water-soluble or water-swellable polymer having a reactive functional group is a polymer compound that has a reactive functional group such as an epoxy, acid chloride, aldehyde or isocyanate group and that absorbs water to swell or form a solution. This water-soluble or water-swellable polymer, when immersed in an aqueous solvent such as physiological saline, a buffer solution, body fluids or blood, absorbs water to swell and the absorbed water will exhibit a lubricating action on the surface of a medical instrument when the latter contacts the wall of a blood vessel. To insure this effect, the water-soluble or water-swellable polymer must have a water absorption of at least 50 wt %, preferably at least 100 wt %, in the range of use temperatures (typically 30°–40° C.).

The water-soluble or water-swellable polymer having a reactive functional group can be produced by copolymerizing a monomer having a reactive functional group in the molecule with a water-soluble monomer. The water-soluble or water-swellable polymer is preferably a block or graft copolymer in which monomers having a reactive functional group aggregate to form a reactive domain whereas water-soluble monomers aggregate to form a hydrophilic domain. Such a block or graft copolymer is preferred since it gives satisfactory results in terms of not only the lubricating action of the hydrogel layer formed on the matrix surface of a medical instrument but also the strength of its adhesion to the matrix surface.

The monomer having a functional group may be exemplified by monomers such as glycidyl acrylate and glycidyl methacrylate that have reactive hetero rings in the molecule, monomers such as acrylic acid chloride and methacrylic acid chloride that have acid chlorides in the molecule, and monomers such as acryloyloxyethyl isocyanate that have an isocyanate group in the molecule. Preferred reactive monomers are glycidyl acrylate and glycidyl methacrylate that have an epoxy group as a reactive group, that permit the reaction to be accelerated by heat and that are fairly easy to handle. The water-soluble monomer may be exemplified by acrylamide or derivatives thereof, vinyl pyrrolidone, acrylic acid, methacrylic acid or derivatives thereof, as well as copolymers or blended compositions of polymers that contain these monomers having a main component, polymers that are composed of monomers having saccharides or phospholipids in side chains, and maleic anhydride modified polymers. Advantageous examples of the water-soluble monomer include N-methyl acrylamide, N,N-dimethyl acrylamide, N,N-diethyl acrylamide, acryloylmorpholine, N,N-dimethylaminoethyl acrylamide, vinyl pyrrolidone, 2-methacryloyloxyethyl phosphorylcholine, 2-methacryloyloxyethyl-D-glycoside, 2-methacryloyloxyethyl-D-mannoside and vinyl methyl ether.

Preferable molar ratio of the reactive polymer B such as GMA having a reactive functional group to the water-soluble polymer A such as DMAA is B:A=1:1–1:100, more preferably 1:5–1:50, most preferably 1:10–1:20.

The water-soluble or water-swellable polymer having reactive functional groups may be heated or otherwise treated so that the reactive functional groups will enter into a crosslinking reaction to become insoluble. The insolubilized polymer, when contacting buffer solution, body fluids or physiological saline, will absorb water to form a hydrogel layer on the surface of the medical instrument. The formed hydrogel layer serves as a "lubricating layer" which prevents direct contact between the surface of the medical instrument and a living tissue, thereby leading to lower friction.

The reactive functional group is preferably an epoxy group that permits the reaction to be easily accelerated by heat. After the water-soluble or water-swellable polymer having an epoxy group in the molecule is coated on a matrix, the latter may be heated at 40° C. and above, whereupon a hydrogel layer will readily form on the surface of the matrix. Heating is effective in increasing the rate at which water-soluble or water-swellable polymers having a reactive functional group react either with themselves or with the matrix surface if it carries a functional group capable of reacting with said reactive functional group. The heating temperature is preferably at least 50° C., more preferably at least 60° C. To accelerate the reaction, heating may be performed in the presence of a catalyst which is advantageously selected from among tertiary amine compounds such as trialkylamine compounds and pyridine if the reactive functional group is an epoxy group. In order to form a tenacious hydrogel layer on the matrix surface, it is important that an intermolecular reaction be carried out with the matrix being thoroughly impregnated with the water-soluble or water-swellable polymer having a reactive functional group.

With a view to improving the endurance of the "lubricating layer" or to controlling its lubricating action, the coating of the water-soluble or water-swellable polymer having a reactive functional group may be subjected to a crosslinking treatment. As a result, a small amount of three-dimensional network structure will form and this helps enhance the durability of the "lubricating layer" without unduly sacrificing its lubricating action. However, care should be exercised in the formation of crosslinks since the overpresence of a crosslinked structure will reduce the tendency to swell upon water absorption, thereby impairing the low friction of the matrix surface. Any common crosslinking techniques are applicable, as exemplified by polymer crosslinking with active radicals being generated upon exposure to light, heat or radiations, optionally accomplished by the addition of polymerizable polyfunctional monomers, coating with polyfunctional crosslinking agents, and the crosslinking of functional groups within the molecule in the presence of a catalyst such as a polyamino, polyhydroxy or a polyaldehyde compound.

The preferred degree of the crosslinking(curing) of the polymer or mixture thereof is 50% or more, more preferably 80% or more, most preferably 95% or more of the reacting ratio of the epoxy group calculated by the peak strength of epoxy group measured by ATR-IR method.

[2] In the second aspect of the invention, the matrix surface of a medical instrument swells in a solvent and forms an interpenetrating network structure with the water-soluble or water-swellable polymer or the macromonomer, thereby insuring that said polymer or macromonomer will be securely fixed onto the matrix. The interpenetrating network structure suffices to be formed at the interface between the matrix and the polymer or macromonomer layer. By increasing the strength of the interfacial bond, one can form a surface lubricating layer having high peel resistance.

One example of the interpenetrating network structure is a structure of crosslinking between molecules formed by the mutual reaction of the reactive groups such as epoxy groups of the water-swellable polymer in a matrix surface of a medical instrument such as urethane polymer.

The matrix of the medical instrument may be of the same kind as used in the first aspect of the invention. Additionally, it may be of any kind that will swell in solvents on the condition that it should have high mechanical strength and that it should not experience significant dimensional changes. A preferred matrix and solvent combination is such that the water-soluble or water-swellable polymer or macromonomer can be coated under conditions such that the percent swelling calculated by the following equation (1) is 1–100%, preferably 5–40%, more preferably 10–30%:

$$\text{Percent swelling} = \frac{\Delta W/\text{the density of solvent}}{Wo/\text{the density of matrix}} \times 100 \quad (1)$$

The specific procedure of measuring the percent swelling is as follows:

(1) The matrix of a medical instrument is cut to a sheet measuring 1 cm×3 cm×0.3 mm (the weight of the sheet is Wo) and then immersed in 25 ml of a solvent;

(2) the sheet is recovered from the solvent and the residual solvent is immediately wiped off the surface and the change in the weight of the sheet ($\Delta W$) is calculated.

The matrix may be immersed in the solvent for any length of time if its dimensions will not change significantly and if the required physical properties will be retained. From an operational viewpoint, the immersion time ranges generally from 1 second to 10 minutes, preferably from 10 seconds to 5 minutes, more preferably from 30 seconds to 3 minutes.

There is no need for the matrix to contain an alkali metal alcoholate group, an amino group, an alkali metal amido group, a carboxylate group, a sulfonate group, a magnesium halide group or a fluoroborate complex group as long as it swells in the solvent used.

The water-soluble or water-swellable polymer to be used in the second aspect of the invention is the same as what can be used in the first aspect. Alternatively, a macromonomer may be used. The term "macromonomer" as used herein means a compound comprising a backbone with branches and the macromonomer for use in the invention is desirably such that the branches are lubricity exhibiting sites whereas the backbone is a site having domains that are crosslinked or rendered to have an increased molecular weight upon heating. Specific examples of the macromonomer that may be used in the invention include a macromonomer of glycidyl methacrylate and dimethyl acrylamide, a macromonomer of glycidyl methacrylate and a maleic anhydride/hydroxyethyl methacrylate copolymer, and a macromonomer of glycidyl methacrylate and a maleic anhydride/acrylamide copolymer.

[3] In accordance with the third aspect of the invention, a polymer solution having dissolved in a solvent a mixture of a water-soluble or water-swellable polymer having a reactive functional group and a polymer having a functional group capable of reacting with said reactive functional group is impregnated in the surface of the matrix of a medical instrument and subsequently insolubilized to form a surface lubricating layer on the surface of a medical instrument. Alternatively, a polymer solution having dissolved in a solvent a water-soluble or water-swellable polymer having a reactive functional group is first impregnated in the surface of the matrix of a medical instrument and, subsequently, a polymer solution having dissolved in a solvent a polymer having a functional group capable of reacting with said reactive functional group is impregnated in the matrix surface and the impregnated solutions are insolubilized to form a surface lubricating layer on the surface of the medical instrument.

The matrix of the medical instrument according to the third aspect of the invention may be the same as what is employed in the first aspect of the invention. The water-soluble or water-swellable polymer having a reactive functional group which is to be used in the third aspect of the invention may also be the same as what is employed in the first aspect of the invention.

The polymer having a functional group capable of reacting with the reactive functional group in the first mentioned polymer is one of the polymers and copolymers that are comprised of monomer units having functional groups capable of reacting with said reactive functional group, as exemplified by carboxyl, hydroxyl, amino, carboxylic anhydride and thiol groups. Specific examples include polyethyleneimine, polyacrylic acid, polymethacrylic acid, polyallylamine, polylysine, polyvinyl alcohol, ethylene-vinyl alcohol copolymer, and copolymers of these homopolymers and/or copolymers. Monomers to be copolymerized need not be capable of reacting with the reactive functional group in the first mentioned polymer and may be exemplified by acrylamide derivatives, (meth)acrylate esters, and monomers having phospholipids or saccharides in the molecule. Advantageous examples are copolymers with polymer compounds that exhibit anti-blood coagulating activities (heparin-like activity and anti-thrombin activity) and which are poly(sulfuric acid) compounds such as 2-acrylamide-2-methylpropanesulfonic acid and sulfoalkyl acrylates.

Given a water-soluble or water-swellable polymer alone that has an epoxy group as the reactive functional group of interest, a desired crosslinking reaction will not proceed efficiently. If said polymer is used in combination with a polymer having a hydroxyl or amino group, the crosslinking reaction will be accelerated to enable the formation of a tenacious surface lubricating layer. An epoxy group reacts with a hydroxy, an amino or certain other groups, so a copolymer of a monomer having an epoxy group in the molecule and a monomer having a hydroxyl, carboxyl, amino or another group that reacts with the epoxy group in the molecule is difficult to synthesize because said copolymer will undergo reaction within the molecule to become insoluble. However, according to the third aspect of the invention, a polymer having a carboxyl or amino group and a polymer having an epoxy group are prepared separately and coated onto the matrix surface and this enables the incorporation of a structure having charges on the surface. Using these functional groups, one can insure that antithrombotic agents to be described hereinafter are adsorbed by an electrostatic interaction in such a way that they are fixed to the surface lubricating layer on a medical instrument or that they can be released over time. Needless to say, antithrombotic agents may be impregnated without depending on the electrostatic interaction so as to permit their sustained release.

The amount of the polymer having a (second) functional group capable of reacting with the (first) reactive functional group may be preferably 0.01 to 50, more preferably 0.05 to 20, most preferably 0.1 to 10 parts by weight based on 100 parts by weight of the water-soluble or water-swellable polymer having a (first) reactive functional group.

[4] The matrix of the medical instrument according to the fourth aspect of the invention may be the same as what is used in the first aspect. The polymer that is to be dissolved in a solvent together with the water-soluble or water-swellable polymer is preferably the same as the polymer of which the matrix of the medical instrument is made. To insure good solubility and high dimensional stability, the polymer may be replaced by one component present in the polymer of which the matrix is made. Particularly in the case of a medical instrument the matrix of which is made of a multi-layered shaped part, the polymer or a component thereof that are to be dissolved in a solvent are preferably the same as the polymer that composes the outermost surface of the matrix of the medical instrument or a component thereof. If a polymer of the same type as the matrix or a component in the polymer comprising the matrix is added to a polymer that exhibits surface lubricity when wetted, a surface lubricating layer will form that is improved in the adhesion to the matrix or which has greater strength. Considering the solubility of the matrix and the ease of handling, the solvent to be used may be a mixed type.

The amount of the polymer of the same type as the matrix or the component in the polymer comprising the matrix may be preferably 0.01 to 50, more preferably 0.05 to 20, most preferably 0.1 to 10 parts by weight based on 100 parts by weight of the water-soluble or water-swellable polymer having a reactive functional group.

The water-soluble or water-swellable polymer to be used in the fourth aspect of the invention may be the same as the polymer that can be used in the first aspect. If desired, a maleic anhydride based polymer may also be employed. The maleic anhydride based polymer may be a homopolymer of maleic anhydride but a copolymer of methyl vinyl ether and maleic anhydride is used with particular advantage. An example of this copolymer is "GANTREZ AN" which is commercially available from G.A.F. Corporation and which consists of methyl vinyl ether and maleic anhydride at a molar ratio of substantially 1:1. Derivatives of the maleic anhydride based polymer are not limited to those which are soluble in water and insolubilized products may be used as long as they contain the maleic anhydride based polymer as a chief component and if they exhibit surface lubricity when wetted.

The solution having the two kinds of polymer dissolved therein need be coated onto a medical instrument only once but in order to further increase the layer that exhibits surface lubricity, two or more coatings are preferably applied. Stated more specifically, the first coating is applied from a solution that has a high content of the chief component of the polymer that composes the matrix of a medical instrument and the content of the polymer that exhibits surface lubricity when wetted is increased in the second and subsequent coatings, thereby providing a gradient in the physical properties of the overall coating layer. The coating layer formed by this method adheres strongly to the matrix of the medical instrument and will exhibit outstanding lubricity on the outermost layer.

[5] The water-soluble or water-swellable polymer to be used in the fifth aspect of the invention may be the same as what is used in the fourth aspect. If desired, the water-soluble or water-swellable polymer having a reactive functional group may be mixed with a hydrophilic polymer that reacts with said reactive functional group, for example, a hydrophilic polymer that contains a monomer having a carboxyl, hydroxyl, amino, carboxylic anhydride, thiol or some other group that reacts with an epoxy group if said reactive functional group is an epoxy group, and the two polymers are reacted with each other to form an insolubilized surface lubricating layer.

The modified polyolefin is a copolymer (random, block or graft) of an olefin such as ethylene or propylene and another monomer or it may be an olefin-based polymer alloy. Examples of the monomer that can be copolymerized with olefins include maleic anhydride, acrylic acid or derivatives thereof, methacrylic acid or derivatives thereof, vinyloxysilane, keteneacetal, dioxolane and vinyl acetate.

The polymer that will adhere to polyolefins may be selected from among polymers commercially available as polyolefin adhesive polymers, as well as those polymers synthesized for providing enhanced compatibility with or adhesion to polyolefins. Satisfactory adhesion will be exhibited by copolymers of polyolefins with monomers such as maleic anhydride, ethyl acrylate, acrylic acid, methacrylic acid and glycidyl methacrylate, vinyl chloride and vinyl acetate.

The polymer that will adhere to modified polyolefins may be exemplified by the above-listed modified polyolefins including those which have the same structure as the matrix of a medical instrument.

The surface lubricating layer which covers the outer surface of a medical instrument is heated or otherwise treated to insure that reactive functional groups in the polymer water-soluble or water-swellable react with themselves to form intermolecular crosslinks. The crosslinked water-soluble or water-swellable polymer, when contacting body fluids or physiological saline, absorbs water to swell and form a hydrogel layer having lubricating action.

If the modified polyolefin forming the matrix of a medical instrument or the adhesive polymer forming the adhesive layer has functional groups capable of reacting with the water-soluble or water-swellable polymer which will form a surface lubricating layer, said polymer will react with the modified polyolefin or adhesive polymer to form a tenacious surface lubricating layer. Even if the matrix of the medical instrument is made of a polyolefin having no functional groups capable of reacting with the water-soluble or water-swellable polymer, the use of an adhesive polymer in the adhesive layer that will adhere to that polyolefin insures that the surface lubricating layer which is chiefly composed of the water-soluble or water-swellable polymer will have increased resistance to exfoliation.

To form the adhesive layer, coextrusion or coating may be employed to have the adhesive polymer be present preliminarily on the matrix of a medical instrument or, alternatively, the adhesive polymer may be dissolved in a solvent together with the water-soluble or water-swellable polymer, with the resulting solution being subsequently applied onto the matrix of the medical instrument. In order to assure that the adhesive polymer has increased resistance to exfoliation from the matrix of the medical instrument, the adhesive polymer is desirably dissolved in a solvent that swells the matrix, with the resulting solution being subsequently applied to cover the matrix surface. Examples of the solvent that can swell the matrix include toluene, xylene, benzene, tetrahydrofuran, dioxane, hexane, methylene chloride and mixed solvents based on these solvents. Suitable solvents and coating conditions are selected in accordance with the properties of the specific matrix used.

If the medical instrument is a dilating catheter balloon, the surface lubricating layer need not be formed over the entire surface of the balloon but may be formed in selected areas such as the tapered portion at the tip or base of the balloon. Particularly in the case of dilating a blood vessel, it is preferred that the surface lubricating layer should not be applied to the entire part of the balloon considering the need for retention at the target site. On the other hand, if the medical instrument is to be used to administer a drug (antithrombotic agent) with a view to preventing reconstriction of the dilated blood vessel, the surface lubricating layer is preferably formed on the entire part of the balloon.

The matrix of a catheter balloon needs only to have a polyolefin or modified polyolefin layer on the surface and it may be a multi-layered balloon or a metal-containing balloon. In the former case, the overlying layers may be formed of polyesters, polyamides, polyphenylene sulfite, polyether sulfone, polyimides, etc. in order to provide higher pressure resistance or to produce a balloon of a non-compliant type which will experience limited deformation under pressure.

Additionally, in order to enhance the strength and capability of the surface lubricating layer, the application of the adhesive layer or the surface lubricating layer may be repeated several times.

With a view to providing improved antithrombotic action, the surface lubricating layer (hydrogel layer) in the first to the fifth aspect of the invention may be treated with antithrombotic agents in such a way that they are carried on that layer or can be released over time. Any antithrombotic agents may be used as long as they can inhibit the formation of thrombi or hydrolyze the formed thrombi and they include but are not limited to both natural and synthetic substances, as typified by anticoagulants, platelet inhibitors and fibrinolysis accelerators. More specific examples include: heparin, low-molecular weight heparin, dermatan sulfate, heparan sulfate, activated protein C, hirudin, aspirin, thrombomodulin, DHG, plasminogen activators (streptokinase and urokinase), aprotinin, nafamostat mesilate (FUT), gabexate mesilate (FOY) and various other protease inhibitors in the coagulation system.

Antithrombotic agents may be applied to the matrix of a medical instrument by various methods; a solution containing both an antithrombotic agent and a polymer forming a surface lubricating layer may be applied or, alternatively, a solution containing a polymer forming a surface lubricating layer and a solution containing an antithrombotic agent may be applied separately. If desired, a solution containing an antithrombotic agent may be mixed with a non-antithrombotic such as a polymer substance that provides satisfactory adhesion to the matrix, thereby insuring efficient coating applications on the matrix surface or controlling the rate at which the antithrombotic agent will be released over time. If a polymer solution containing both an antithrombotic agent and a polymer capable of forming a surface lubricating layer is applied onto the matrix surface, a surface having not only the antithrombotic action but also the surface lubricity can be formed in such a way that the antithrombotic agent will be released over time. Such a dual surface can also be formed by first applying an antithrombotic agent onto the matrix surface of a medical instrument and then applying a polymer capable of forming a surface lubricating layer.

Antithrombotic agents are considered to function by one of the following two mechanisms and either mechanism may be utilized in the present invention. In one mechanism, the antithrombotic agent as held on the hydrogel layer on the matrix surface is released slowly to exhibit the antithrombotic action; in the other mechanism, the antithrombotic agent is bound to the reactive functional groups in the molecule of the water-soluble or water-swellable polymer, whereby it is immobilized in the hydrogel layer to exhibit the inherent function.

To measure surface lubricity (frictional resistance), a sheet is prepared which has the same surface as a specific medical instrument and set in a tester of the construction shown in FIG. 1. The detailed test conditions are shown in Examples described below. A convenient way to evaluate surface lubricity is by rubbing the surface of the sheet with fingers. A low-friction surface having the water-soluble or water-swellable polymer bound thereto of the present invention is characterized by a slimy feel similar to that of an eel and has a static friction coefficient of no more than 0.15, which is equivalent to an initial frictional resistance of no more than 150 gf as determined in contact with a polyethylene film on the tester shown in FIG. 1.

Medical instruments that are required to have low friction and antithrombotic properties may advantageously be exemplified by catheters and guide wires which are intended for use within blood vessels. Other examples include:

1) catheters such as stomach catheter, feeding tube, and ED tube which are inserted via the mouth or nose into the stomach and at times left indwelling therein;

2) tubes or cuffs of oxygen catheters, oxygen cannulas, and windpipes, tubes and cuffs of tracheotomy tubes, and catheters such as intratracheal aspiration catheters which are inserted via the mouth or nose into the windpipe and at times left indwelling therein;

3) catheters such as catheters and balloons in urethral catheters, urinal catheters, and balloon catheters which are inserted into the urethra or the ureter and at times left indwelling therein;

4) catheters such as suction catheters, fluid discharge catheters, and rectal catheters which are inserted into various body cavities, organs or tissues and at times left indwelling therein;

5) catheters such as indwelling needles, IVH catheters, thermodilution catheters, angiographic catheters, vasodilating catheters, dilators, or introducers which are inserted into or left indwelling in blood vessels and guide wires and stylets for such catheters;

6) inspection and therapeutic devices for insertion into various internal organs, as well as contact lenses, etc.;

7) stents, as well as artificial blood vessels, windpipes, bronchial tubes, etc.; and 8) medical devices (e.g. artificial hearts, lungs and kidneys) for use in extracorporeal circulatory treatments, and associated circuits.

The following examples are provided for the purpose of further illustrating the present invention but are in no way to be taken as limiting.

EXAMPLE 1

Triethylene glycol was added dropwise to adipic acid dichloride at 50° C.; thereafter, hydrochloric acid was distilled off by evaporation for 3 h at 50° C. Methyl ethyl ketone was added to the resulting oligoester and the mixture was added dropwise to a solution comprising sodium hydroxide, 31% hydrogen peroxide, surfactant dioctyl phosphate and water and reaction was carried out at −5° C. for 20 min. The reaction product was washed repeatedly with water and methanol and subsequently dried to yield a polyperoxide (PPO) having a plurality of peroxide groups in the molecule. With the PPO used as a polymerization initiator, glycidyl methacrylate (GMA) was polymerized in vacuo under stirring at 80° C. for 2 h with benzene being and a solvent. The reaction product was reprecipitated with diethyl ether to yield poly-GMA having peroxide groups in the molecule. With the poly-GMA being used as a polymerization initiator, dimethyl acrylamide (DMAA) as a hydrophilic monomer was dissolved in DMSO and subjected to polymerization at 80° C. for 18 h to yield a block copolymer having poly-GMA in reactive domains and poly-DMAA in water-swellable hydrophilic domains. Analysis by $^1$H-NMR showed that the block copolymer consisted of DMAA and GMA at a molar ratio.

A 10 wt % dimethyl formamide solution of polyurethane (PELLETHANE 65D of Du Pont) containing 1 wt % of a protease inhibitor, ethyl p-(6-guanidinohexanoyl) benzoate methanesulfonate, was applied to a polyurethane catheter having an outside diameter of 5 Fr (5×0.33 mm). Subsequently, a 2% acetone solution of a block copolymer consisting of DMAA and GMA at a molar ratio of 6.8:1 was coated over the polyurethane layer and reaction was carried out at 60° C. for 18 h. Drops of physiological saline were placed on the surface of the catheter, which was touched with fingers to examine its lubricity. It was found to be a slimy low-frictions surface. The lubricity of the surface was not lost even when it was rubbed vigorously by 20 times of pressure application with a fingertip.

EXAMPLE 2 AND COMPARATIVE EXAMPLE 1

A block copolymer of DMAA and GMA (mol. ratio=6.8:1) as prepared in Example 1 was dissolved at a concentration of 2 wt % in methyl ethyl ketone. The resulting solution was applied to a catheter having an outside diameter of 5 Fr and reaction was carried out in an oven at 60° C. for 8 h. The catheter was immersed in physiological saline and rubbed with fingers; it was found to have a very slippery, low-friction surface compared to an untreated catheter (Comparative Example 1).

The catheter was then immersed in a solution of low-molecular weight heparin (500 units/ml) for 5 min. and freeze-dried. This heparinized catheter of Example 2 was immersed in a fresh sample of human blood for 5 min. and no thrombus was found to adhere to the surface of the catheter.

EXAMPLE 3

Two parts by weight of a block copolymer of the same type as prepared in Example 1 (DMAA:GMA mol. ratio=10.1:1) and one part by weight of catalyst pyridine were dissolved in 1,4-dioxane. A sheet (1 cm×3 cm×0.3 mm) of polyurethane (PELLETHANE 75D of Dow Chemical) was immersed in the resulting solution for 30 sec. The sheet was found to swell by 25%. The swollen sheet was allowed to react at 60° C. for 18 h and thereafter washed with water to form a surface that would exhibit lubricity when wetted. Surface analysis by ATR-IR showed that instead of the peak for an epoxy group present in the sample before the coating operation, the peak for an ether bond was present, demonstrating the crosslinking of epoxy groups.

The thus treated sheet was immersed in physiological saline or water and it exhibited outstanding lubricity. Additionally, the sheet was subjected to boiling for 1 h and yet it exhibited the same degree of lubricity as it did before boiling; the sheet was thus verified to have outstanding durability.

Subsequently, the sheet was immersed in the aqueous solution including low molecular heparin 500 unit/ml, for 5 minutes, then the sheet was freeze-dried to form a heparin-immobilized sheet. The thus obtained heparin-immobilized sheet was immersed in human fresh blood for 5 minutes and the adhesion of any thrombus could not be observed on the sheet.

COMPARATIVE EXAMPLE 2

A closed reactor was charged with GMA (10 g) as it was dissolved in solvent dimethyl sulfoxide (90 g). After azobisisobutyronitrile (0.05 g) was added as an initiator, reaction was carried out in vacuo at 80° C. for 18 h. The reaction product was purified with diethyl ether (poor solvent) and tetrahydrofuran (good solvent); by NMR-IR, the refined product was verified to be a GMA homopolymer. Similarly, DMAA (10 g) as dissolved in dimethyl sulfoxide (90 g) was polymerized and the product was found to be a DMAA homopolymer.

The two kinds of polymer each weighing 2 parts by weight were dissolved in 1,4-dioxane and a sheet (1 cm×3 cm×0.3 mm) of polyurethane (PELLETHANE 75D of Dow Chemical) was immersed in the resulting solution for 30 sec. The sheet was found to swell by 25%. The swollen sheet was allowed to react at 60° C. for 18 h and thereafter washed with water to form a surface that would exhibit lubricity when wetted. Surface analysis by ATR-IR showed that instead of the peak for an epoxy group present in the sample before the coating operation, the peak for an ether bond was present, demonstrating the crosslinking of epoxy groups.

The thus treated sheet was immersed in physiological saline or water and it exhibited outstanding lubricity. However, when the sheet was subjected to boiling for 1 h, its lubricity was practically lost; the sheet was thus verified to have only low durability.

EXAMPLE 4

Two parts by weight of a block copolymer of the same type as prepared in Example 1 and one part by weight of catalyst pyridine were dissolved in tetrahydrofuran and a sheet (1 cm×3 cm×0.3 mm) of an ethylene-vinyl acetate copolymer (EVATATE of Sumitomo Chemical Co., Ltd.) for 1 min. The sheet was found to swell by 15%. The swollen sheet was allowed to react at 60° C. for 18 h and thereafter washed with water to form a surface that would exhibit lubricity when wetted. Surface analysis by ATR-IR showed that instead of the peak for an epoxy group present in the sample before the coating operation, the peak for an ether bond was present, to demonstrating the crosslinking of epoxy groups.

The thus treated sheet was immersed in physiological saline or water and it exhibited outstanding lubricity. Additionally, the sheet was subjected to boiling for 1 h and yet it exhibited the same degree of lubricity as it did before boiling; the sheet was therefore verified to have outstanding durability.

COMPARATIVE EXAMPLE 3

A solution of two polymers was prepared as in Comparative Example 2 and an EVATATE sheet (1 cm×3 cm×0.3 mm) was immersed in the solution for 1 min. The sheet was found to swell by 15%. the swollen sheet was allowed to react at 60° C. for 18 h and thereafter washed with water to form a surface which would exhibit lubricity when wetted. Surface analysis by ATR-IR showed that instead of the peak for an epoxy group present in the sample before the coating operation, the peak for an ether bond was present, demonstrating the crosslinking of epoxy groups.

The thus treated sheet was immersed in physiological saline or water and it exhibited outstanding lubricity. However, when the sheet was subjected to boiling for 1 h, its lubricity was practically lost; the sheet was thus verified to have only low durability.

EXAMPLE 5

A closed reactor was charged with DMAA (10 g), iodoacetic acid (chain transfer agent; 1 g) and t-butyl peroctoate (initiator; 0.05) and reaction was performed in vacuo at 80° C. for 8 h to yield polymer (1) identified below. Five grams of this polymer (1) and 1 g of GMA were dissolved in 90 g of benzene and allowed to react in a nitrogen atmosphere at 60° C. for 8 h in the presence of a small quantity of hydroquinone. The reaction product was purified with diethyl ether (poor solvent) and tetrahydrofuran (good solvent) to yield polymer (2) also identified below. By NMR, the product was verified to have a macromonomeric structure of the same type as possessed by polymer (2).

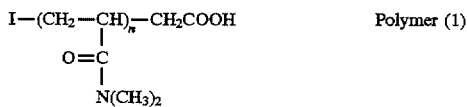

Polymer (1)

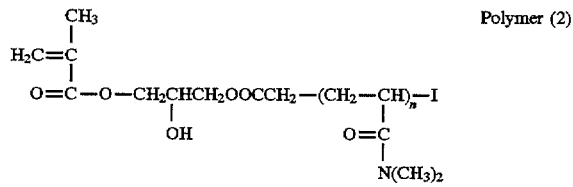

Polymer (2)

Two parts by weight of polymer (2) and 0.01 part by weight of initiator azobisisobutyronitrile were dissolved in chloroform and a sheet (1 cm×3 cm×0.3 mm) of ethylene-vinyl chloride copolymer (RYURON E of Tosoh Corp.) was immersed in the resulting solution for 30 sec. The sheet was found to swell by 19%. The swollen sheet was allowed to react at 60° C. for 18 h and thereafter washed with water to form a surface that would exhibit lubricity when wetted. Surface analysis by ATR-IR showed the disappearance of the carbon-carbon double bonds present in the sample before the coating operation, demonstrating the formation of a polymer.

The thus treated sheet was immersed in physiological saline or water and it exhibited outstanding lubricity. Additionally, the sheet was subjected to boiling for 1 h and yet it exhibited the same degree of lubricity as it did before boiling; the sheet was thus verified to have outstanding durability.

Subsequently, the sheet was immersed in the aqueous solution including low molecular heparin 500 unit/ml, for 5 minutes, then the sheet was freeze-dried to form a heparin-immobilized sheet. The thus obtained heparin-immobilized sheet was immersed in human fresh blood for 5 minutes and the adhesion of any thrombus could not be observed on the sheet.

COMPARATIVE EXAMPLE 4

Two polymers of the same types as prepared in Comparative Example 2 were dissolved in chloroform. A sheet (1 cm×3 cm×0.3 mm) of an ethylene-vinyl chloride copolymer (RYURON E of Tosoh Corp.) was dissolved in the resulting solution for 30 sec. The sheet was found to swell by 19%. The swollen sheet was allowed to react at 60° C. for 18 h and thereafter washed with water to form a surface that would exhibit lubricity when wetted. Surface analysis by ATR-IR showed that instead of the peak for an epoxy group present in the sample before the coating operation, the peak for an ether bond was present, demonstrating the crosslinking of epoxy groups.

The thus treated sheet was immersed in physiological saline or water and it exhibited outstanding lubricity. However, when the sheet was subjected to boiling for 1 h, its lubricity was practically lost; the sheet was thus verified to have only low durability.

EXAMPLE 6

A closed reactor was charged with GMA (9.8), maleic anhydride (14.2 g) and azobisisobutyronitrile (initiator; 0.05 g) as they were dissolved in solvent dimethyl sulfoxide (90) and reaction was performed in vacuo at 80° C. for 18 h. The reaction product was purified with diethyl ether (poor solvent) and tetrahydrofuran (good solvent) to yield a polymer. By NMR and IR, the polymer was verified to contain epoxy groups in the molecule.

Two parts by weight of this polymer and one part by weight of solvent pyridine were dissolved in tetrahydrofuran and a sheet (1 cm×3 cm×0.3 mm) of ethylene-methyl methacrylate copolymer (ACRIFT of Sumitomo Chemical Co., Ltd.) was immersed in the resulting solution for 30 sec. The sheet was found to swell by 25%. The swollen sheet was allowed to react at 60° C. for 18 h. After the reaction, maleic anhydride was subjected to ring opening in ethanol in the presence of sulfuric acid as a catalyst and a sample was prepared by subsequent alkali washing with sodium hydrogencarbonate in physiological saline. Surface analysis by ATR-IR showed that instead of the peak for an epoxy group present in the sample before the coating operation, the peak for an ether bond was present, demonstrating the crosslinking of epoxy groups.

The thus treated sheet was immersed in physiological saline or water and it exhibited outstanding lubricity. Additionally, the sheet was subjected to boiling for 1 h and yet it exhibited the same degree of lubricity as it did before boiling; the sheet was therefore verified to have outstanding durability.

COMPARATIVE EXAMPLE 5

A poly-GMA was prepared as in Comparative Example 2. In a separate step, a closed reactor was charged with monomeric maleic anhydride (5 g) and camphorquinone (photosensitizer; 0.1 g) as they were dissolved in solvent benzene (50 g). After UV irradiation, reaction was carried out in vacuo at 80° C. for 18 h. The reaction product was purified with diethyl ether (poor solvent) and tetrahydrofuran (good solvent) to yield a polymer that would exhibit lubricity when wetted. By NMR and IR, the polymer was verified to be a homopolymer of maleic anhydride.

The two polymers each weighing 2 parts by weight were dissolved in tetrahydrofuran and a sheet (1 cm×3 cm×0.3 mm) of ethylene-methyl methacrylate copolymer (ACRIFT of Sumitomo Chemical Co., Ltd.) was immersed in the resulting solution for 30 sec. The sheet was found to swell by 25%. The swollen sheet was allowed to react at 60° C. for 18 h. After the reaction, maleic anhydride was subjected to ring opening in ethanol in the presence of sulfuric acid as a catalyst and a sample was prepared by subsequent alkali washing with sodium hydrogencarbonate in physiological saline. Surface analysis by ATR-IR showed that instead of the peak for an epoxy group present in the sample before the coating operation, the peak for an ether bond was present, demonstrating the crosslinking of epoxy groups.

The thus treated sheet was immersed in physiological saline or water and it exhibited outstanding lubricity. However, when the sheet was subjected to boiling for 1 h, its lubricity was practically lost; the sheet was thus verified to have only low durability.

COMPARATIVE EXAMPLE 6

Two parts by weight of a macromonomer as prepared in Example 5 and 0.01 part by weight of azobisisobutyronitrile as an initiator were dissolved in methanol and a sheet (1 cm×3 cm×0.3 mm) of ethylene-vinyl chloride (RYURON E of Tosoh Corp.) was immersed in the resulting solution for 30 sec. The sheet was found to swell by 0.5%. The swollen sheet was allowed to react at 60° C. for 18 h. After the reaction, the sheet was washed with water. The lubricity that was exhibited initially decreased as the washing progressed. Thus, the sheet was found to have only low durability.

COMPARATIVE EXAMPLE 7

Two parts by weight of a polymer as prepared in Example 6 and 1 part by weight of pyridine as a catalyst were dissolved in methanol and a sheet (1 cm×3 cm×0.3 mm) of ethylene-methyl methacrylate copolymer (ACRIFT of Sumitomo Chemical Co., Ltd.) was immersed in the resulting solution for 30 sec. The sheet was found to swell by 0.8%. The swollen sheet was allowed to react at 60° C. for 18 h.

After the reaction, maleic anhydride was subjected to ring opening in ethanol in the presence of sulfuric acid as a catalyst and a sample was prepared by subsequent alkali washing with sodium hydrogencarbonate in physiological saline. The sample exhibited lubricity right after the alkali washing but as it progressed, the lubricity decreased, indicating the low durability of the sheet.

EXAMPLE 7

Block copolymer (B1) having a DMAA:GMA molar ratio of 7.1:1 was prepared as in Example 1. Similarly, block copolymer (B2) was prepared by repeating the procedure of Example 1, except that GMA was replaced by hydroxyethyl methacrylate (HEMA); B2 had a DMAA:HEMA molar ratio of 6.4:1.

Block copolymers (B1) and (B2) were each dissolved at 3% in THF (containing 1 wt % pyridine). The two polymer solutions were mixed at a weight ratio of 1:1. A polyurethane tube having an outside diameter of 5 Fr (1.65 mm) was immersed in the mixed solution, dried and allowed to react in an oven at 60° C. for 18 h. The tube was then immersed in physiological saline and rubbed with fingers; it was found to have a slippery, low-friction surface compared to an untreated tube.

EXAMPLE 8

Block copolymers (B1) and (B2) used in Example 7 were each dissolved at 1 wt % in chloroform (containing 1 wt % pyridine). A sheet (200 µm thick) of ethylene-acrylate ester-maleic anhydride terpolymer (BONDINE TX 8030 of Sumika-CDF Kagaku K.K.) was immersed in the resulting solution at 25° C. for 1 min., dried and allowed to react in an oven at 60° C. for 18 h to prepare a sample.

The sample sheet had a hydrogel surface layer that became slimy to exhibit outstanding lubricity when wetted. The surface lubricity of the sheet was evaluated with a tester of the construction shown in FIG. 1.

Method of Testing Surface Lubricity

As shown in FIG. 1 an aqueous environment 1 within a water tank 15, a cylindrical brass weight 2 weighing 1 kg having polyethylene sheet 3 placed on the contacting surface with a test sheet 4 was placed gently on a test sheet 4 adhered to a plastic plate inclined at 30°; the weight was slid repeatedly 100 times at a speed of 100 cm/min. over the sheet across a width of 1 cm and the resulting change in frictional resistance was measured. The final frictional resistance which occurred after 100 slides was calculated to determine an index of surface lubricity. The change in frictional resistance (delta frictional resistance) was calculated by the following equation (A) to determine an index of sustained lubricity:

$$\Delta \text{ frictional resistance} = \begin{pmatrix} \text{Final} \\ \text{frictional} \\ \text{resistance} \end{pmatrix} - \begin{pmatrix} \text{initial} \\ \text{frictional} \\ \text{resistance} \end{pmatrix} \quad (A)$$

The results were 74 gf for the final frictional resistance and no more than 10 gf for the delta frictional resistance; thus, the sample sheet prepared in Example 8 exhibited a consistent low-friction property even after 100 slides. The surface of the sheet and a cross section thereof were examined under a scanning electron microscope (JSM 840 of JEOL LTD.); since no changes occurred as a result of the sliding test, it was verified that the surface lubricating layer was bound firmly to the sheet matrix without separating.

COMPARATIVE EXAMPLES 8 and 9

The untreated sheet in Example 7 (Comparative Example 8) and a sheet that was treated with a THF solution having dissolved therein only the block copolymer (B2) of Example 7 (Comparative Example 9) were tested as in Example 8 to determine frictional resistance. The sheet of Comparative Example 8 did not have an effective lubricating surface (initial frictional resistance: 250 gf; Δ frictional resistance: 15 gf); the sheet of Comparative Example 9 had a surface lubricating layer that did not exhibit a lasting effect (initial frictional resistance: 92 gf; Δ frictional resistance: 110 gf).

EXAMPLE 9

A 10 wt % dimethyl formamide solution of polyurethane (PELLETHANE 65D of Du Pont) containing 1 wt % of a protease inhibitor, ethyl p-(6-guanidinohexanoyl) benzoate methanesulfonate, was applied to a polyurethane catheter having an outside diameter of 5 Fr to prepare a thrombolytic surface capable of not only suppressing the activation of the blood coagulating system by inhibition of thrombin and other coagulation factors but also suppressing platelet aggregation. Subsequently, the catheter was immersed in a mixed solution of block copolymers (B1) and (B2) as in Example 7, dried and allowed to react at 60° C. for 18 h to prepare a catheter having a lubricating surface. Drops of water were placed on the surface of the catheter to evaluate its lubricating property; it was found to be a slimy, low-friction surface. The lubricity of the surface was not even when it was rubbed vigorously by 20 times of pressure application with a fingertip.

To test for its thrombolytic action, the catheter was cut to a length of 30 cm and the tip was immersed in a fresh sample of human blood. After 5 min. of immersion, the surface of the catheter was examined and no clot formation occurred. However, clot was found to adhere to the surface of an untreated polyurethane catheter (control).

EXAMPLE 10

A guide wire was fabricated which was coated with a resin that had tungsten incorporated in polyurethane (TECOFLEX EG-100 A-V of Thermedix Inc.) as a sensitizer in an amount of 50 wt %. A block copolymer consisting of DMAA and GMA at a molar ratio of 6.8:1 as in Example 7 and a random copolymer of methacrylic acid and 2-methacryloyloxyethyl phosphorylcholine (mol. ratio=1:4) were dissolved at respective concentrations of 2 wt % and 1 wt % in THF (containing 1 wt % pyridine). The guide wire was immersed in the resulting polymer solution at 25° C. for 30 sec, dried and allowed to react in an oven at 60° C. for 40 h. The treated guide wire was immersed in physiological saline and rubbed with fingers; it was verified to have a slippery, low-friction surface compared to an untreated guide wire. The treated guide wire was also immersed in a fresh sample of human blood for 5 min. but no clot was found to adhere to the guide wire.

EXAMPLE 11

A block copolymer consisting of DMAA and GMA at a molar ratio of 6.8:1 as in Example 7 and polyethyleneimine (mol. wt.=4000) were dissolved at respective concentrations of 2 wt % and 0.5 wt % in THF (containing 1 wt % pyridine). A guide wire as prepared in Example 10 was immersed in the resulting polymer solution at 25° C. for 30 sec, dried and allowed to react in an oven at 60° C. for 40 h. Subsequently, the guide wire was immersed in a phosphate buffer solution containing 0.2 wt % heparin for 2 min., washed with water and dried to prepare a heparinized surface. The thus treated guide wire had no clot adhering to the surface even when it was immersed in a fresh sample of human blood for 5 min.

EXAMPLE 12

A polyurethane tube as used in Example 7 was immersed for 30 sec in a 2 wt % solution of the DMAA-GMA block copolymer of Example 7 (DMAA:GMA mol ratio=7.1:1) in methyl chloride (containing 1 wt % pyridine) and dried at 60° C. for 2 min. Subsequently, the polyurethane tube was immersed in a 2 wt % solution of a block copolymer of 2-acrylamide-2-methylpropanesulfonic acid (AMPS) and acrylic acid (AA) at a molar ratio of 5:1 in water (containing 1 wt % pyridine), dried at 60° C. for 18 h and allowed to react. The thus treated tube was immersed in physiological saline and rubbed with fingers; it was found to have a slippery, low-friction surface compared to an untreated tube. The treated tube was also immersed in a fresh sample of human blood for 5 min. but no clot was found to adhere to the tube.

EXAMPLE 13

Two parts by weight of a DMAA:GMA block copolymer as prepared in Example 1 (DMAA:GMA mol. ratio=10.1:1), 0.5 parts by weight of an ethylene-acrylate ester-maleic anhydride terpolymer (BONDINE AX8390 of Sumika-CDF Kagaku K.K.) and 1 part by weight of catalyst pyridine were dissolved in chloroform. A BONDINE AX8390 sheet was immersed in the resulting chloroform solution for 1 min. to form a coating of polymers. The coating was then allowed to react at 60° C. for 18 h. After the reaction, the sheet was washed with water to prepare a sample.

The sample sheet was immersed in physiological saline or water and it exhibited outstanding lubricity. Additionally, the sheet was subjected to boiling for 1 h and yet it exhibited the same degree of lubricity as it did before boiling; the sheet was thus verified to have outstanding durability.

Subsequently, the sheet was immersed in the aqueous solution including low molecular heparin 500 unit/ml, for 5 minutes, then the sheet was freeze-dried to form a heparin-immobilized sheet. The thus obtained heparin-immobilized sheet was immersed in human fresh blood for 5 minutes and the adhesion of any thrombus could not be observed on the sheet.

EXAMPLE 14

Two parts by weight of a block copolymer as used in Example 13, 0.5 parts by weight of an acrylate ester which was a component of BONDINE AX8390 and 1 part by weight of catalyst pyridine were dissolved in chloroform. A BONDINE AX8390 sheet was immersed in the resulting chloroform solution for 1 min. to form a polymer coating, which was then allowed to react at 60° C. for 18 h. After the reaction, the sheet was washed with water to prepare a sample.

The sample sheet was immersed in physiological saline or water and it exhibited outstanding lubricity. Additionally, the sheet was subjected to boiling for 1 h and yet it exhibited the same degree of lubricity as it did before boiling; the sheet was thus verified to have outstanding durability.

EXAMPLE 15

Two parts by weight of methyl vinyl ether-maleic anhydride copolymer (GANTREZ AN of G.A.F. Corporation) and 0.5 parts by weight of ethylene-acrylate ester-methacrylic acid terpolymer (NUCLEL AN 4213C of Mitsui-DuPont Co., Ltd.) were dissolved in chloroform. A NUCLEL AN 4213C sheet was immersed in the resulting solution for 30 sec to form a coating of polymers. The coating was then allowed to react at 60° C. for 18 h. After the reaction, maleic arthydride was subjected to ring opening in ethanol in the presence of sulfuric acid as a catalyst, followed by alkali washing with sodium hydrogencarbonate in physiological saline to prepare a sample.

The sample sheet was immersed in physiological saline or water and it exhibited outstanding lubricity. Additionally, the sheet was subjected to boiling for 1 h and yet it exhibited the same degree of lubricity as it did before boiling; the sheet was thus verified to have outstanding durability.

COMPARATIVE EXAMPLE 10

Two parts by weight of GANTREZ AN which was the same polymer as used in Example 15 was dissolved in chloroform. A NUCLEL AN 4213C sheet was immersed in the resulting chloroform solution for 30 sec to form a coating, which was allowed to react at 60° C. for 18 h. After the reaction, maleic anhydride was subjected to ring opening in ethanol in the presence of sulfuric acid as catalyst, followed by alkali washing with sodium hydrogencarbonate in physiological saline to prepare a sample.

The thus treated sheet was immersed in physiological saline or water and it exhibited outstanding lubricity. However, when the sheet was subjected to boiling for 1 h, its lubricity was practically lost; the sheet was thus verified to have only low durability.

EXAMPLE 16

A closed reactor was charged with GMA (2.0 g), maleic anhydride (8.0 g) and initiator azobisisobutyronitrile (0.05 g) as they were dissolved in solvent dimethyl sulfoxide (90 g) and reaction was performed in vacuo at 80° C. for 18 h. The reaction product was purified with diethyl ether (poor solvent) and tetrahydrofuran (good solvent) to yield a polymer that would exhibit lubricity when wetted.

Two parts by weight of this polymer, 0.5 parts by weight of polyurethane (PELLETHANE of Dow Chemical) and 1 part by weight of catalyst pyridine were dissolved in tetrahydrofuran. A polyurethane sheet was immersed in the resulting tetrahydrofuran solution for 30 sec to form a coating of polymers. The coating was then allowed to react at 60° C. for 18 h. After the reaction, maleic anhydride was subjected to ring opening in ethanol in the presence of sulfuric acid as a catalyst, followed by alkali washing with sodium hydrogencarbonate in physiological saline to prepare a sample.

The sample sheet was immersed in physiological saline or water and it exhibited outstanding lubricity. Additionally, the sheet was subjected to boiling for 1 h and yet it exhibited the same degree of lubricity as it did before boiling; the sheet was thus verified to have outstanding durability.

EXAMPLE 17

A block copolymer of the same type as used in Example 13, an ethylene-acrylate ester-maleic anhydride terpolymer (BONDINE AX8390 of Sumika-CDF Kagaku K.K.) and catalyst pyridine were dissolved in chloroform at the concentrations shown in Table 1 below to prepare chloroform solutions. A BONDINE AX8390 sheet was immersed in chloroform solution 1 for 1 min. and the coating was allowed to react at 60° C. for 18 h. Thereafter, the sheet was immersed in chloroform solution 2 and similarly subjected to reaction under heating. The sheet was then washed with water to prepare a sample.

The sample sheet was immersed in physiological saline or water and it exhibited outstanding lubricity. Additionally, the sheet was subjected to boiling for 1 h and yet it exhibited the same degree of lubricity as it did before boiling. The sheet was thus verified to have outstanding durability.

TABLE 1

| Solution No. | Block copolymer content, parts by weight | BONDINE content, parts by weight | Pyridine content, parts by weight |
|---|---|---|---|
| 1 | 0.5 | 1.5 | 1.0 |
| 2 | 1.0 | 1.0 | 1.0 |

EXAMPLE 18

A block copolymer of the same type as used in Example 17, an acrylate ester which was a component of BONDINE AX8390 and catalyst pyridine were dissolved in chloroform at the concentrations shown in Table 2 below to prepare three chloroform solutions. A BONDINE AX8390 sheet was immersed in chloroform solution 1 for 1 min. and the coating was allowed to react at 60° C. for 18 h. Thereafter, the sheet was immersed in chloroform solution 2 and similarly subjected to reaction under heating. The sheet was additionally treated with chloroform solution 3 in a similar manner. The sheet was then washed with water to prepare a sample.

The sample sheet was immersed in physiological saline or water and it exhibited outstanding lubricity. Additionally, the sheet was subjected to boiling for 1 h and yet it exhibited the same degree of lubricity as it did before boiling. The sheet was thus verified to have outstanding durability.

TABLE 2

| Solution No. | Block copolymer content, parts by weight | Acrylate ester content, parts by weight | Pyridine content, parts by weight |
|---|---|---|---|
| 1 | 0.5 | 1.5 | 1.0 |
| 2 | 1.0 | 1.0 | 1.0 |
| 3 | 1.5 | 0.5 | 1.0 |

EXAMPLE 19

A methyl vinyl ether-maleic anhydride copolymer (GANTREZ AN of G.A.F. Corporation) and an ethylene-acrylate ester-methacrylic acid terpolymer (NUCLEL AN4123C of Mitsui-DuPont Co., Ltd.) were dissolved in chloroform at the concentrations shown in Table 3 below to prepare three chloroform solutions. A NUCLEL AN4213C sheet was immersed in chloroform solution 1 for 1 min. and the coating was allowed to react at 60° C. for 18 h. Thereafter, the sheet was immersed in chloroform solution 2 and similarly subjected to reaction under heating. The sheet was additionally treated with chloroform solution 3 in a similar manner. After the reaction, maleic acid was subjected to ring opening in ethanol in the presence of sulfuric acid as a catalyst, followed by alkali washing with sodium hydrogencarbonate in physiological saline to prepare a sample.

The sample sheet was immersed in physiological saline or water and it exhibited outstanding lubricity. Additionally, the sheet was subjected to boiling for 1 h and yet it exhibited the same degree of lubricity as it did before boiling. The sheet was thus verified to have outstanding durability.

TABLE 3

| Solution No. | GANTREZ AN content, parts by weight | NUCLEL content, parts by weight |
|---|---|---|
| 1 | 0.5 | 1.5 |
| 2 | 1.0 | 1.0 |
| 3 | 1.5 | 0.5 |

COMPARATIVE EXAMPLE 11

GANTREZ AN which was the same copolymer as used in Example 19 was dissolved in 1.5 parts by weight in chloroform. A NUCLEL AN 4213C sheet was immersed in the resulting chloroform solution for 30 sec and the coating was allowed to react at 60° C. for 18 h. This procedure was repeated two more times. After the reaction, maleic anhydride was subjected to ring opening in ethanol in the presence of sulfuric acid as a catalyst, followed by alkali washing with sodium hydrogencarbonate in physiological saline to prepare a sample. The sample sheet was immersed in physiological saline or water and it exhibited outstanding lubricity. However, when the sheet was subjected to boiling for 1 h, its lubricity was practically lost; the sheet was thus verified to have only low durability.

EXAMPLE 20

A copolymer as prepared in Example 16 and polyurethane (PELLETHANE of Dow Chemical), as well as catalyst pyridine were dissolved in tetrahydrofuran at the concentrations shown in Table 4 below to prepare three THF solutions. A polyurethane sheet was immersed in THF solution 1 for 30 sec and the coating was allowed to react at 60° C. for 18 h. Thereafter, the sheet was immersed in THF solution 2 and similarly subjected to reaction under heating. The sheet was additionally treated with THF solution 3 in a similar manner. After the reaction, maleic anhydride was subjected to ring opening in ethanol in the presence of sulfuric acid as a catalyst, followed by alkali washing with sodium hydrogencarbonate in physiological saline to prepare a sample.

The sample sheet was immersed in physiological saline or water and it exhibited outstanding lubricity. Additionally, the sheet was subjected to boiling for 1 h and yet it exhibited the same degree of lubricity as it did before boiling. The sheet was thus verified to have outstanding durability.

TABLE 4

| Solution No. | Copolymer content, parts by weight | PELLETHANE content, parts by weight | Pyrine content, parts by weight |
| --- | --- | --- | --- |
| 1 | 0.5 | 1.5 | 1.0 |
| 2 | 1.0 | 1.0 | 1.0 |
| 3 | 1.5 | 0.5 | 1.0 |

EXAMPLE 21

(Preparation of the Matrix of Catheter Balloon)

Figure 2:
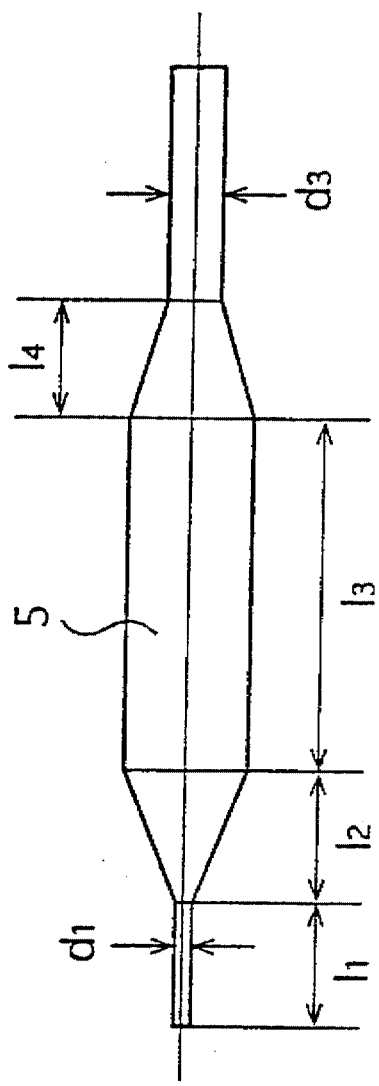
FIG. 2 shows the shape of a catheter balloon, as seen from the front and a lateral side, according to an embodiment of the invention (length is shown in mm)
Figure 2:
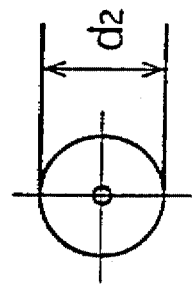

A modified polyolefin (acrylic acid modified polyethylene available under the trade name "A221M" from Mitsubishi Petrochemical Co., Ltd.) was shaped to a tube having an outside diameter of 1.1 mm and an inside diameter of 0.7 mm. The tube was biaxially drawn for orientation to make a balloon of the shape and dimensions shown in FIG. 2. Stated more specifically, the tube was first stretched axially, set in a mold having a cavity complying with the shape of an inflated balloon, and supplied with pressure to inflate radially to a balloon shape ($d_1$=0.6 mm, $d_2$=3 mm, $d_3$=1.5 mm; $l_1$=5 mm, $l_2$=5 mm, $l_3$=20 mm, $l_4$=4 mm).

(Synthesis of Water-Soluble or Water-Swellable Polymer)

The procedure of Example 1 was repeated to synthesize a block copolymer consisting of dimethyl acrylamide (DMAA) and glycidyl methacrylate (GMA) at a molar ratio of 6:1.

(Preparation of Surface Lubricated Catheter Balloon)

The separately prepared balloon matrix was immersed in a chloroform/toluene (1:1 by weight ratio) solution containing 1% of modified polyolefin (ethylene-acrylate ester-maleic anhydride terpolymer available under the trade name "BONDINE AX-8390" from Sumika-CDF Kagaku K.K.), 2% of a block copolymer DMAA/GMA and 1% catalyst pyridine for 1 min. and dried in an oven at 60° C. for 18 h.

Subsequently, the balloon was immersed in the aqueous solution including low molecular heparin 500 unit/ml, for 5 minutes, then the balloon was freeze-dried to form a heparin-immobilized balloon. The thus obtained heparin-immobilized balloon was immersed in human fresh blood for 5 minutes and the adhesion of any thrombus could not be observed on the balloon.

(Methods of Evaluating Surface Lubricity)

Figure 4:
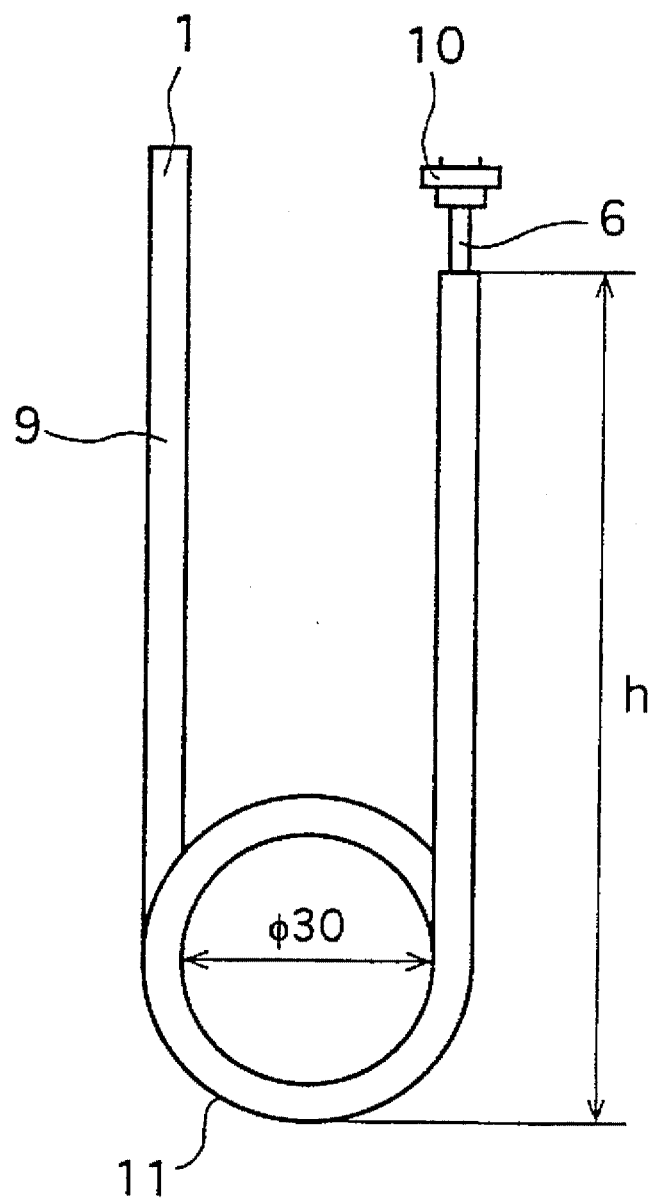
FIG. 4 shows schematically a test method for evaluating the surface lubricity as achieved by the invention (length is shown in mm)
Figure 5:
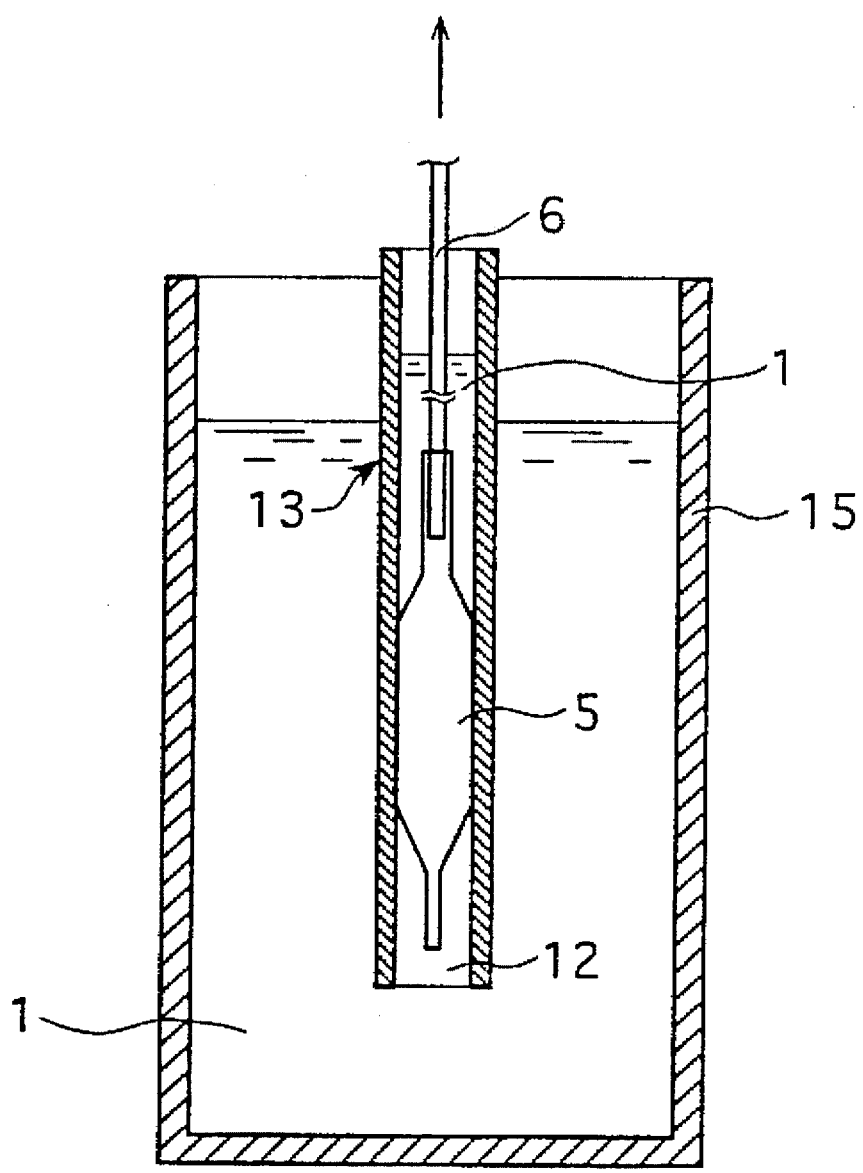
FIG. 5 shows schematically another test method for evaluating the surface lubricity as achieved by the invention.

The surface lubricity of the catheter balloon was evaluated by the following indices by the test methods as shown in FIGS. 4 and 5: frictional resistance as an index of balloon accessibility to a constricted portion of a blood vessel (target site); pull-out resistance as an index of balloon retention in the constricted portion (target site); and differential frictional resistance (delta frictional resistance) as an index of the lasting quality of surface lubricity.

Figure 3:
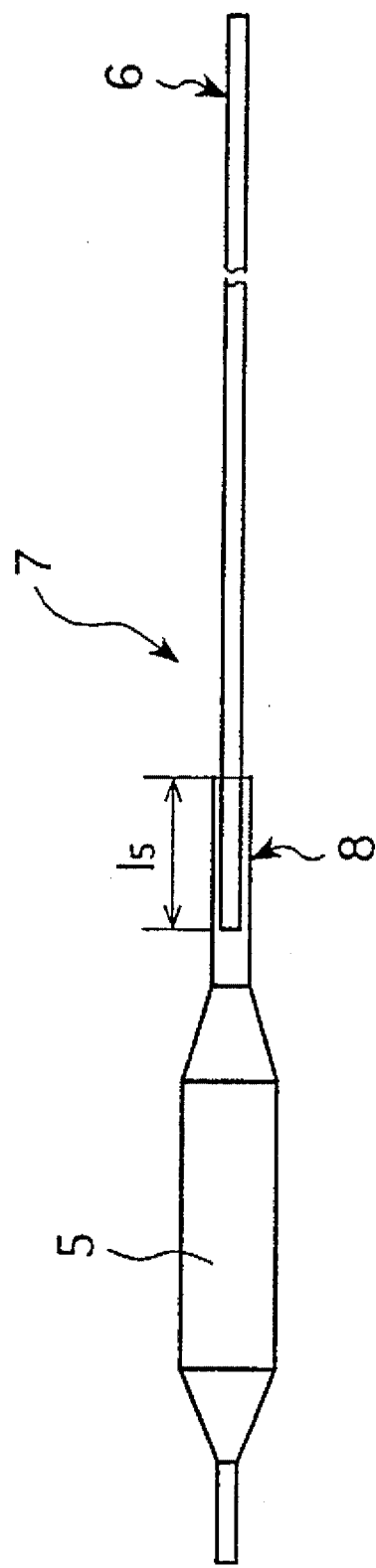
FIG. 3 is a front view of a catheter constructed by bonding the catheter balloon to the tip of a shaft (length is shown in mm)

(1) Frictional Resistance 30 parts by weight of polypropylene (HIPOLE F401 of Mitsui Petrochemical Industries, Ltd.) and 70 parts by weight of polybutene (BYURON of Mitsui Petrochemical Industries, Ltd.) were kneaded in a twin-screw mixer and a shaft indicated by 2 in FIG. 3 was molded, which had an inside diameter of 0.85 mm and an outside diameter of 1.00 mm. The separately prepared balloon 5 was bonded to the tip of the shaft, thereby fabricating a catheter 7 ($l_5$=15 mm). Then, as shown in FIG. 4, a polyethylene pipe 11 having an inside diameter of 3 mm and an outside diameter of 5 mm was wound in one turn (i.d. 30 mm) and a half and this loop portion of the pipe 11 was filled with water to form a channel 9 (h=200 mm) that simulated a blood vessel system in the living body. With the balloon 5 folded back, catheter 7 was inserted into the channel 9 and set up in such a way that the tip of the balloon was located at the terminal end of the loop. The end of the shaft 6 was set in the load cell 10 of an autograph (Model AGS-100A of Shimadzu Corp.) and the balloon 5 was reciprocated 100 times over a stroke of 10 mm in the polyethylene pipe 11. The value of resistance as measured right after the end of 100 strokes was taken as the final frictional resistance (gf). The result is shown in Table 5.

Conditions of Measurement

| Load cell | 5 kgf |
| --- | --- |
| Stroke length | 10 mm |
| Stroke speed | 100 mm/min. |
| Number of strokes | 100 |

Δ frictional resistance

Delta frictional resistance was calculated by eq. (A) and the result is shown in Table 5:

$$\Delta \text{ frictional resistance} = \left( \begin{array}{c} \text{Final} \\ \text{frictional} \\ \text{resistance} \end{array} \right) - \left( \begin{array}{c} \text{initial} \\ \text{frictional} \\ \text{resistance} \end{array} \right) \quad (A)$$

(2) Pull-out Resistance

As shown in FIG. 5, a channel 12 was constructed of a polyethylene pipe 13 (i.d. 3 mm; o.d. 5 mm) as it was submerged in water 1 in a water tank 15. As in (1), catheter 7, with balloon 5 folded back, was inserted into channel 12 and pressure was supplied into the balloon so that it inflated to be retained within the channel 12. The end of the shaft 6 was set in the load cell (not shown) of an autograph (Model AGS-100A of Shimadzu Corp.) and a maximum pull-out resistance (gf) was measured. The result is shown in Table 5.

Conditions of Measurement

| Load cell | 5 kgf |
| --- | --- |
| Crosshead speed | 10 mm/min. |
| Balloon inflating pressure | 8 kg/cm² |

EXAMPLE 22

A balloon treated by the same method as used in Example 21 was immersed in a THF solution containing 2% DMAA- GMA block copolymer (6:1) and 1% catalyst pyridine and dried in an oven at 60° C. for 18 h. The thus treated balloon was evaluated by the same methods as in Example 21 and the results are also shown in Table 5.

EXAMPLE 23

The matrix of a balloon as prepared in Example 21 was immersed in a toluene/dimethylformamide (4:1 in weight ratio) solution containing a modified polyolefin of the same type as used in Example 21 (BONDINE AX-8390; 2%) at 50° C. for 2 min. and dried in an oven at 60° C. for 1 h. Subsequently, the matrix was immersed in a THF solution containing 2% of a DMAA-GMA block copolymer as synthesized in Example 21 and 1% of catalyst pyridine for 1 min. and dried in an oven at 60° C. for 18 h. The thus treated balloon was evaluated by the same methods as in Example 21 and the results are also shown in Table 5.

COMPARATIVE EXAMPLE 12

The matrix of a balloon as prepared in Example 21 was not given any surface treatments but immediately evaluated by the same methods as in Example 21. The results are shown in Table 5.

EXAMPLE 24

A tube made of linear low-density polyethylene (ZF260-1 of Tosoh Corp.) was shaped to a balloon as in Example 21 and crosslinked by exposure to 30 Mrad of electron beams (500 kV). The prepared balloon matrix was immersed for 1 min. in a chloroform/toluene (1:1 by weight ratio) solution containing 1% of a modified polyolefin (BONDINE AX-8390) as used in Example 21, 2% of a DMAA-GMA block copolymer as synthesized in Example 21 and 1% of catalyst pyridine and dried in an oven at 60° C. for 18 h. The thus treated balloon was evaluated by the same methods as in Example 21 and the results are shown in Table 5.

EXAMPLE 25

A balloon matrix as prepared in Example 24 was immersed in a toluene/dimethylformamide (4:1 by weight ratio) solution containing 2% of the same modified polyolefin as used in Example 21 at 50° C. for 2 min. and dried in an oven at 60° C. for 1 h. Subsequently, the matrix was immersed in a THF solution containing 2% of a DMAA-GMA block copolymer as synthesized in Example 21 and 1% of catalyst pyridine and dried in an oven at 60° C. for 18 h. The thus treated balloon was evaluated by the same methods as in Example 21 and the results are shown in Table 5.

COMPARATIVE EXAMPLE 13

A balloon matrix as prepared in Example 24 was not given any surface treatments but immediately evaluated by the same methods as in Example 21. The results are shown in Table 5.

TABLE 5

| Sample | Matrix | Frictional resistance, gf Final | Δ | Pull-out resistance, gf |
|---|---|---|---|---|
| Ex. 21 | modified polyolefin | 8.7 | 0.5 | 246 |
| Ex. 22 | modified polyolefin | 8.3 | 0.3 | 234 |
| Ex. 23 | modified polyolefin | 8.5 | 0.6 | 269 |
| Ex. 24 | linear low-density polyethylene | 8.5 | 0.6 | 270 |
| Ex. 25 | linear low-density polyethylene | 9.4 | 0.5 | 280 |
| Comp. Ex. 12 | modified polyolefin | 21.4 | 0.5 | 456 |
| Comp. Ex. 13 | linear low-density polyethylene | 20.6 | 0.9 | 470 |

What is claimed is:

1. A medical instrument exhibiting surface lubricity when wetted, comprising a surface coated with a surface lubricating layer, said surface lubricating layer comprising a block or graft copolymer having a hydrophilic domain and a reactive domain, said reactive domain having a reactive functional group selected from the group consisting of epoxy and isocyanate, and wherein said functional group is cross-linked with another functional group.

2. A medical instrument according to claim 1, wherein said surface lubricating layer further comprises a polymer having a functional group selected from the group consisting of a carboxyl group, an amino group, a hydroxyl group, and a maleic anhydride group.

3. A medical instrument exhibiting surface lubricity when wetted, comprising a matrix material surfaced with a surface lubricating layer comprising a block or graft copolymer having a hydrophilic domain and a reactive domain, said reactive domain having a reactive functional group selected from the group consisting of an epoxy group and an isocyanate group, wherein said surface lubricating layer is formed by dipping the matrix material in a solution of said block or graft copolymer; and wherein said functional group is cross-linked with another functional group to form an interpenetrating network structure between the matrix material and the copolymer.

4. A medical instrument according to claim 1, wherein said surface lubricating layer further comprises an anti-thrombotic agent.

5. A medical instrument according to claim 1, wherein the molar ratio of said hydrophilic domains to said reactive domains is 1:50.

6. A medical instrument according to claim 1, wherein said surface lubricating layer is formed by coating said block or graft copolymer on the surface of the medical instrument; and heating said coating to at least 40° C.

7. A medical instrument according to claim 3, wherein the swelled ratio of the matrix surface is within the range of 1 to 100% as defined by equation (1):

$$\text{Percent swell} = \frac{\Delta W/\text{density of the solution}}{W_o/\text{density of the matrix surface}} \times 100 \quad (1)$$

wherein $W_o$=the weight of the matrix material before dipping the matrix material into the solution; and $\Delta W$=the increased weight of the matrix material after dipping into the solution.

* * * * *

UNITED STATES PATENT AND TRADEMARK OFFICE
CERTIFICATE OF CORRECTION

PATENT NO. : 5,670,558

DATED : September 23, 1997

INVENTOR(S) : Makoto ONISHI et al

It is certified that error appears in the above-identified patent and that said Letters Patent is hereby corrected as shown below:

In Column 15, line 22, delete "0.05" and insert -- 0.05 g --.

In Column 16, line 28, delete "90" and insert -- 90 g --.

Signed and Sealed this

Twenty-fourth Day of March, 1998

Attest:

BRUCE LEHMAN

*Attesting Officer*                *Commissioner of Patents and Trademarks*